United States Patent
Hung

(10) Patent No.: US 9,956,202 B2
(45) Date of Patent: May 1, 2018

(54) USE OF INDOLYL AND INDOLINYL HYDROXAMATES FOR TREATING NEURODEGENERATIVE DISORDERS OR COGNITIVE DECICITS

(71) Applicant: Taipei Medical University, Taipei (TW)

(72) Inventor: Kuo Sheng Hung, Taipei (TW)

(73) Assignee: Taipei Medical University, Taipei (TW)

( * ) Notice: Subject to any disclaimer, the term of this patent is extended or adjusted under 35 U.S.C. 154(b) by 0 days. days.

(21) Appl. No.: 15/038,671

(22) PCT Filed: Nov. 24, 2014

(86) PCT No.: PCT/US2014/067040
§ 371 (c)(1),
(2) Date: May 23, 2016

(87) PCT Pub. No.: WO2015/077685
PCT Pub. Date: May 28, 2015

(65) Prior Publication Data
US 2016/0303079 A1    Oct. 20, 2016

Related U.S. Application Data

(60) Provisional application No. 61/908,168, filed on Nov. 24, 2013.

(51) Int. Cl.
| | |
|---|---|
| A61K 31/404 | (2006.01) |
| A61K 45/06 | (2006.01) |
| A61K 31/04 | (2006.01) |
| A61K 31/122 | (2006.01) |
| A61K 31/355 | (2006.01) |
| A61K 31/37 | (2006.01) |
| A61K 31/375 | (2006.01) |
| A61K 31/4365 | (2006.01) |
| A61K 31/519 | (2006.01) |
| A61K 31/616 | (2006.01) |
| A61K 9/00 | (2006.01) |

(52) U.S. Cl.
CPC .......... *A61K 31/404* (2013.01); *A61K 9/0053* (2013.01); *A61K 31/04* (2013.01); *A61K 31/122* (2013.01); *A61K 31/355* (2013.01); *A61K 31/37* (2013.01); *A61K 31/375* (2013.01); *A61K 31/4365* (2013.01); *A61K 31/519* (2013.01); *A61K 31/616* (2013.01); *A61K 45/06* (2013.01)

(58) Field of Classification Search
CPC .................................................... A61K 31/404
See application file for complete search history.

(56) References Cited

U.S. PATENT DOCUMENTS

| | | | | |
|---|---|---|---|---|
| 6,187,805 B1 * | 2/2001 | Pineiro | ................ | A61K 31/404 514/235.2 |
| 2011/0245315 A1 * | 10/2011 | Chen | .................... | C07D 209/08 514/415 |

FOREIGN PATENT DOCUMENTS

| | | |
|---|---|---|
| WO | 2013040520 | 3/2013 |
| WO | 2013055386 | 4/2013 |
| WO | 2013150529 | 10/2013 |

OTHER PUBLICATIONS

Jackowski, British Journal of Neurosurgery 9 (1995): 303-317.*
Savaskan et al., Current Neuropharmacology 13 (2015): 1-8.*
Miotto et al., Arq. Neuro-Psiquiatr 69 (2011): 1-8.*
European patent office search report dated Jun. 7, 2017 for counterpart application No. 14864113.7.
Chuang et al., Multiple roles of HDAC inhibition in neurodegenerative conditions, Trends in Neuroscience, Elsevier, Amsterdam, NL, vol. 32, No. 11, 2009, pp. 591-601.
Lee et al., 1-Arysulfonyl-5-(N-hydroxyacrylamide)indolines Histone Deacetylase Inhibitors Are Potent Cytokine Release Suppressors, Chembiochem—A European Journal of Chemical Biology., vol. 14, No. 10, 2013, pp. 1248-1254.

* cited by examiner

*Primary Examiner* — Robert C Hayes
(74) *Attorney, Agent, or Firm* — WPAT, P.C., Intellectual Property Attorneys; Anthony King

(57) ABSTRACT

The present invention relates to novel use of indolyl and indolinyl hydroxamates. Particularly, the invention relates to use of indolyl and indolinyl hydroxamates in the manufacturing a medicament or a pharmaceutical composition for treating a ischemic and hemorrhagic stroke, spinal cord injury, cranial nerve injury, peripheral nerve injury and a neurodegenerative disorder or cognitive deficit.

11 Claims, 12 Drawing Sheets

(D)

(B)

(C)

USE OF INDOLYL AND INDOLINYL HYDROXAMATES FOR TREATING NEURODEGENERATIVE DISORDERS OR COGNITIVE DECICITS

FIELD OF THE INVENTION

The present invention relates to novel use of indolyl and indolinyl hydroxamates. Particularly, the invention relates to use of indolyl and indolinyl hydroxamates in the manufacturing a medicament or a pharmaceutical composition for treating a ischemic and hemorrhagic stroke, spinal cord injury, cranial nerve injury, peripheral nerve injury and a neurodegenerative disorder or cognitive deficit.

BACKGROUND OF THE INVENTION

Neurodegenerative disorders (NDs) are a group of related human maladies that share a common pathophysiological feature, the progressive degeneration of selective neuronal populations over the course of time. These neurodegenerative diseases include but are not limited to Alzheimer's disease and related dementias, Parkinson's disease, Huntington's disease, Lewy Body Disease and related movement disorders, and Friedrich's Ataxia and related Spinocerebellar Ataxia's. As a result of increases in the elderly population, it is expected that the number of patients with neurodegenerative disorders involving forms of dementia such as Alzheimer's disease will increase. Because these diseases progress with age and affect both the patient and their living environment, it is important to find a therapeutic method at an early stage. Characteristic clinical symptoms of Alzheimer's disease include progressive cognitive deterioration, declining ability to participate in daily activities, neuropsychiatric symptoms, and behavioral changes. Plaques containing misfolded proteins, called beta amyloids, form in the brain many years before the clinical signs of Alzheimer's are observed. Together, these plaques and neurofibrillary tangles form the pathological hallmarks of the disease. These features can only be discovered at autopsy and help to confirm the clinical diagnosis.

Huntington's disease (HD), is an autosomal dominant neurodegenerative disease whose symptoms are caused by the loss of cells in the basal ganglia of the brain. This damage to cells affects cognitive ability (thinking, judgment, memory), movement, and emotional control. HD is characterized by uncontrollable, dancelike movements and personality changes. HD patients develop slurred speech, an unsteady walk and difficulty in swallowing. There is no effective treatment for HD. After a long illness, individuals with HD die from complications such as choking or infection.

Parkinson's disease (PD) is an idiopathic, slowly progressive, degenerative CNS disorder characterized by slow and decreased movement, muscular rigidity, resting tremor, and postural instability. Despite extensive investigations, the cause of PD remains unknown. The loss of substantia nigra neurons, which project to the caudate nucleus and putamen, results in the depletion of the neurotransmitter dopamine in these areas.

Acute and/or chronic neuronal loss in the adult CNS results in the irreversible loss of function due to the very poor ability of mature nerve cells to proliferate and compensate for the lost neurons. Thus attenuating or reducing neuronal loss is essential for preservation of function.

Therefore, there is a need in the related art an agent or a compound to treat a neurodegenerative disease.

SUMMARY OF THE INVENTION

The invention provides a method for treating a neurodegenerative disorder or cognitive deficit in a subject, comprising administering to the subject a therapeutically effective amount of the compound having formula (I) as mentioned below. Accordingly, the invention provides a use of the compound of formula (I) in the manufacture of a medicament for treating a neurodegenerative disorder or cognitive deficit in a subject. Also provided is a compound of formula (I) for use in treating a neurodegenerative disorder or cognitive deficit in a subject. In another aspect, the invention provides a method for treating a ischemic and hemorrhagic stroke, spinal cord injury, cranial nerve injury or peripheral nerve injury in a subject, comprising administering to the subject a therapeutically effective amount of the compound having formula (I) as mentioned below. Accordingly, the invention provides a use of the compound of formula (I) in the manufacture of a medicament for treating a ischemic and hemorrhagic stroke, spinal cord injury, cranial nerve injury or peripheral nerve injury in a subject.

The preferred compound is 3-(1-benzensulfonyl-1H-indol-5-yl)-N-hydroxy-acrylamide. The amount of the compound is administered to the subject by intravenous, intramuscular injection or oral intake at about 1 to 100 mg/Kg body weight of the subject. In one embodiment, the subject is human and the administration amount if the compound is about 1 to about 50 mg/Kg body weight in a human; preferably about 1 to about 30 mg/Kg body weight in a human, preferably, about 1 to about 20 mg/Kg body weight, about 1 to about 10 mg/Kg body weight, about 2 to about 10 mg/Kg body weight, about 2 to about 8 mg/Kg body weight or about 2 to about 10 mg/Kg body weight; more preferably about 3 to about 5 mg/Kg body weight.

The compounds of the invention are particularly effective in the treatment of neurodegenerative disorders or cognitive deficits, particularly, Huntington's disease, Parkinson's disease, dementia and Alzheimer's disease.

DETAILED DESCRIPTION OF THE INVENTION

Figure 1:
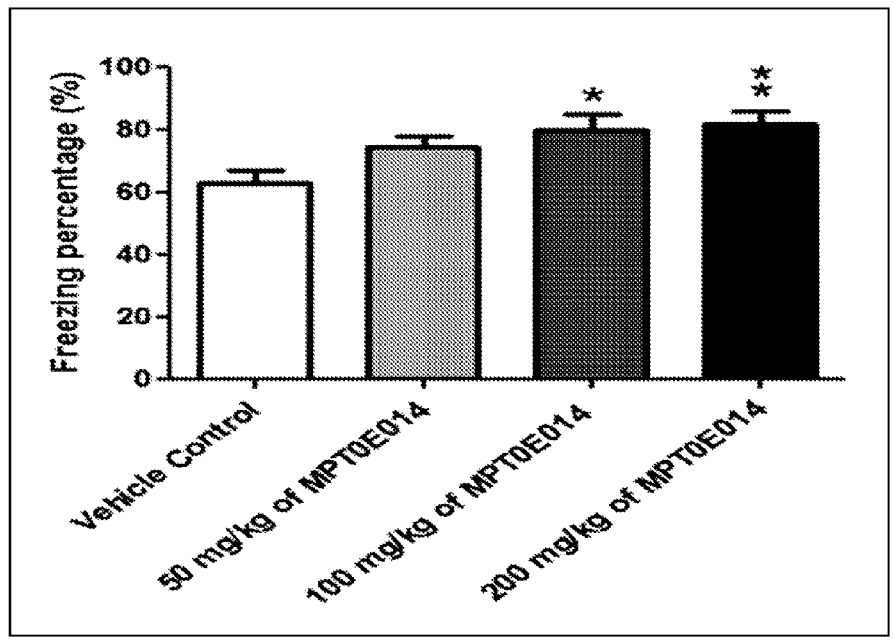
FIG. 1 illustrates the effect of compound 1 on enhancement of memory formation in accordance with one embodiment of this invention.

The present invention is based on the discovery that indolyl and indolinyl hydroxamates are effective in treating a neurodegenerative disorder or cognitive deficit; therefore, these active compounds are potential lead compounds for use as therapeutic agents for the treatment of a neurodegenerative disorder or cognitive deficit, preferably dementia. In addition, the invention found that the above compounds is effective in treating a spinal cord injury.

All scientific and technical terms used in this application have meanings commonly used in the art unless otherwise specified. As used in this application, the following words or phrases have the meanings specified.

As used herein, "a" or "an" means at least one, unless clearly indicated otherwise.

The term "alkyl" refers to a straight or branched monovalent hydrocarbon containing 1-20 carbon atoms (e.g., $C_1$-$C_{10}$). Examples of alkyl include, but are not limited to, methyl, ethyl, n-propyl, i-propyl, n-butyl, i-butyl and tert-butyl. The term "alkenyl" refers to a straight or branched monovalent hydrocarbon containing 2-20 carbon atoms (e.g., $C_2$-$C_{10}$) and one or more double bonds. Examples of alkenyl include, but are not limited to, ethenyl, propenyl, allyl, and 1,4-butadienyl. The term "alkynyl" refers to a straight or branched monovalent hydrocarbon containing 2-20 carbon atoms (e.g., $C_2$-$C_{10}$) and one or more triple bonds. Examples of alkynyl include, but are not limited to, ethynyl, 1-propynyl, 1- and 2-butyryl and 1-methyl-2-butyryl. The term "alkoxyl" refers to an —O-alkyl radical. Examples of alkoxyl include, but are not limited to, methoxy, ethoxy, n-propoxy, isopropoxy, n-butoxy, iso-butoxy, sec-butoxy, and tert-butoxy.

The term "aryl" refers to a monovalent 6-carbon monocyclic, 10-carbon monocyclic, 14-carbon tricyclic aromatic ring system. Examples of aryl groups include, but are not limited to, phenyl, naphthyl, and antracenyl. The term "heteroaryl" refers to a monovalent aromatic 5-8 membered monocyclic, 8-12 membered bicyclic, or 11-14 membered tricyclic ring system having one or more heteroatoms (such as O, N, S, or Se). Examples of heteroaryl groups include, but are not limited to, pyridyl, furyl, imidazolyl, benzimidazolyl, pyrimidinyl, thienyl, quinolinyl, indolyl, tetrazol, and thiazolyl.

Alkyl, alkenyl, alkynyl, aryl, and heteroaryl mentioned above include both substituted and unsubstituted moieties. Possible substituents on aryl and heteroaryl include, but are not limited to, $C_1$-$C_{10}$ alkyl, $C_2$-$C_{10}$ alkenyl, $C_2$-$C_{10}$ alkynyl.

The term "spinal cord injury (SCI)" interrupts conduction of nerve impulses, leading to neurological dysfunction. Primary injury to the spinal cord immediately disrupts cell membranes, destroys myelin and axons in the longitudinal tracts, damages microvessels, and thus triggers devastating secondary injury process with the release of various deleterious factors. Multiple cellular and molecular mechanisms of the secondary injury process cause neurodegeneration, through complex cascades to spread neurodegeneration beyond the site of primary injury. Secondary injury cascades are active biological processes and thus provide a window of opportunity for the treatment of SCI using selective inhibitors. Appropriate treatment strategies targeted to active secondary injury mediators of SCI may protect neuronal cells, and augment axonal regeneration and reconnection.

The phrase "neurodegenerative disorders or cognitive deficits" refers to a disease in which degeneration occurs in either gray or white matter, or both, of the nervous system.

The term "dementia" is defined as a disorder manifest by loss of mental capacity affecting a person's ability to function. Dementing disorders were at one time viewed as of psychiatric origin in the younger population and of "senile" derivation—a consequence of aging—in the elderly. There was little hope in treating either of these. Neurobehavioral deficits, especially impaired cognitive function, are often the cause of significant disability. Hence, compounds that are effective in improving neurobehavioral deficits are potential candidate compounds for manufacturing a medicament or composition for treating dementia.

As used herein, the term "subject" can refer to any warm-blooded mammal including, but not limited to, human beings, pigs, rats, mice, dogs, goats, sheep, horses, monkeys, apes, rabbits, cattle, etc.

The term "treatment" as used herein includes preventative (e.g., prophylactic), curative or palliative treatment; and "treating" as used herein also includes preventative (e.g., prophylactic), curative or palliative treatment.

The term "effective amount" is used throughout the specification to mean an amount or concentration of a compound according to the present invention which is effective within the context of its administration, whether that context produces the desired result of alleviating, reversing or preventing further deterioration of the condition or disease state to be treated. Effective amounts of compounds according to the present invention include those amounts which are effective to enhance and/or increase cognition and/or memory in patients in need.

In one aspect, the invention provides a method for treating a neurodegenerative disorder or cognitive deficit in a subject, comprising administering to the subject a therapeutically effective amount of the compound having formula (I),

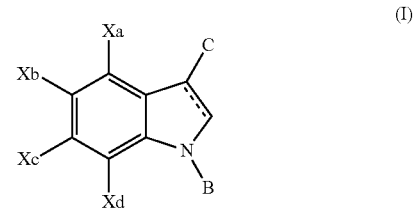

(I)

wherein ═ is a single or double bond; B is R, C(O)R, CH$_2$R, SO$_2$R, SO$_3$R, or SO$_2$NRR'; C is R, C(O)R, CH$_2$R, SO$_2$R, or CH═CHC(O)NHOH; each $X_a$, $X_b$, $X_c$ and $X_d$ are independently R, halogen, nitro, nitroso, OR, or CH═CHC(O)NHOH; and each R and R' are independently H, alkyl, alkenyl, alkynyl, aryl, or heteroaryl. In one example, each C, $X_a$, $X_c$, and $X_d$ are independently H; B is SO$_2$R; and $X_b$ is CH═CHC(O)NHOH, or a pharmaceutically acceptable salt, isomer, prodrug or solvate thereof.

Accordingly, the invention also provides a use of the compound of formula (I) in the manufacture of a medicament for treating a neurodegenerative disorder or cognitive deficit in a subject. Also provided is a compound of formula (I) for use in treating a neurodegenerative disorder or cognitive deficit in a subject.

In another aspect, the invention provides a method for treating a ischemic and hemorrhagic stroke, spinal cord injury, cranial nerve injury or peripheral nerve injury in a subject, comprising administering to the subject a therapeutically effective amount of the compound having formula (I). Accordingly, the invention also provides a use of the compound of formula (I) in the manufacture of a medicament for treating a ischemic and hemorrhagic stroke, spinal cord injury, cranial nerve injury or peripheral nerve injury in a subject. Also provided is a compound of formula (I) for use in treating a ischemic and hemorrhagic stroke, spinal cord injury, cranial nerve injury or peripheral nerve injury in a subject.

In some embodiments, B is $SO_2R$; C is H; each $X_a$, $X_b$, and $X_c$ are independently CH=CHC(O)NHOH; Xd is hydrogen; and R is phenyl or phenyl substituted by F.

Shown below are exemplary compounds, compounds 1-11, of this invention.

compound 1

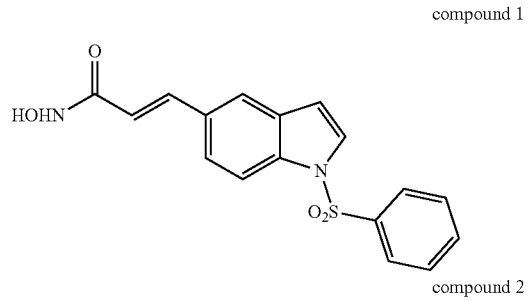

compound 2

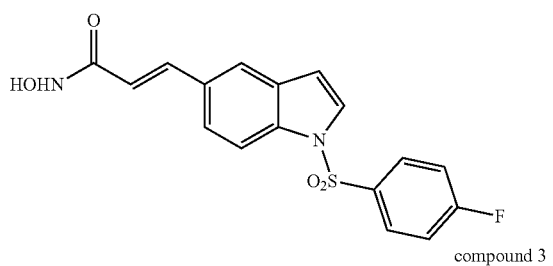

compound 3

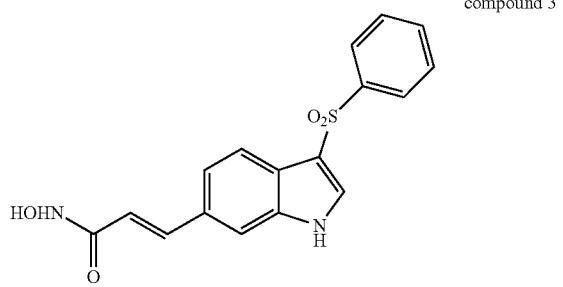

compound 4

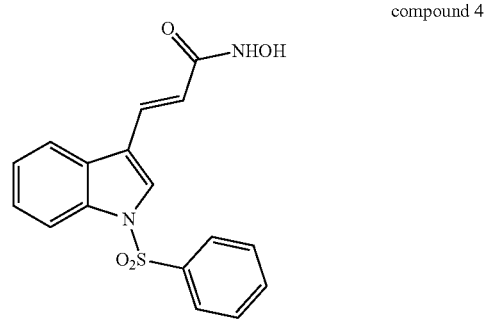

compound 5

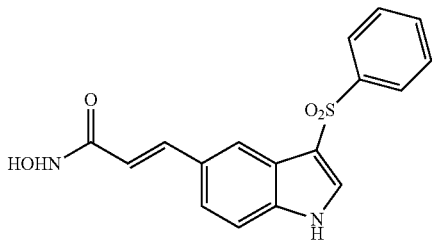

compound 6

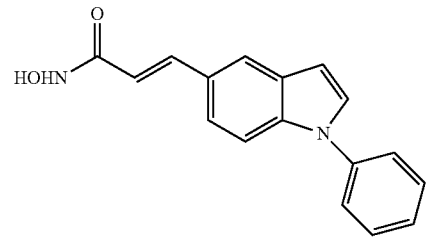

compound 7

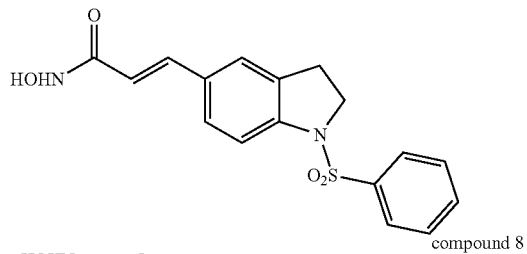

compound 8

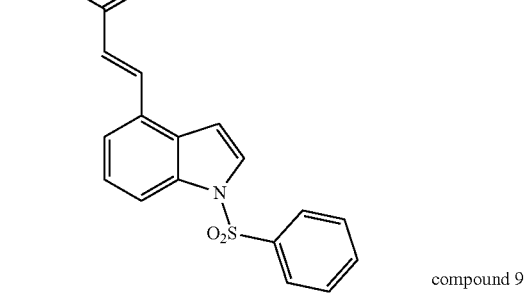

compound 9

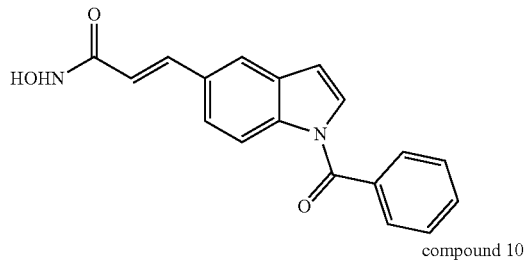

compound 10

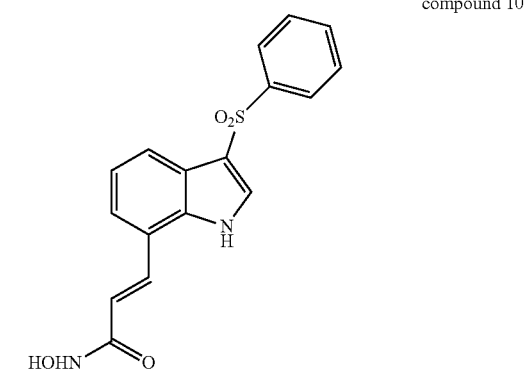

compound 11

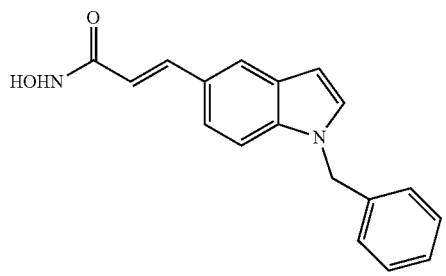

The compounds of this invention, particularly, the compound of formula (I), may be synthesized according to the method described in a U.S. patent application Ser. No. 13/074,312 filed by Chen et al on Mar. 29, 2011; the contents of this prior application is herein incorporated by reference. For example, compound 1 of this invention, 3-(1-benzensulfonyl-1H-indol-5-yl)-N-hydroxy-acrylamide, may be synthesized according to Scheme 2 described by Chen et al.

The method of treating neuronal injury (e.g., dementia or spinal cord injury) includes steps of administering to a subject in need thereof an effective amount of the compound of formula (I) as shown above. In a preferred embodiment, the compound is 3-(1-benzensulfonyl-1H-indol-5-yl)-N-hydroxy-acrylamide.

In one embodiment, the subject may be a mammal, preferably a human.

In some embodiments, the neurodegenerative disorders or cognitive deficits includes, but is not limited to, diseases of central motor systems including degenerative conditions affecting the basal ganglia (Huntington's disease, Wilson's disease, striatonigral degeneration, corticobasal ganglionic degeneration), Tourette's syndrome, Parkinson's disease, progressive supranuclear palsy, progressive bulbar palsy, familial spastic paraplegia, spinomuscular atrophy, ALS and variants thereof, dentatorubral atrophy, olivo-pontocerebellar atrophy, paraneoplastic cerebellar degeneration, and dopamine toxicity; diseases affecting sensory neurons such as Friedreich's ataxia, diabetes, peripheral neuropathy, and retinal neuronal degeneration; diseases of limbic and cortical systems such as cerebral amyloidosis, Pick's atrophy, and Retts syndrome; neurodegenerative pathologies involving multiple neuronal systems and/or brainstem including dementia, Alzheimer's disease, Parkinson's disease, AIDS-related dementia, Leigh's disease, diffuse Lewy body disease, epilepsy, multiple system atrophy, Guillain-Barre syndrome, lysosomal storage disorders such as lipofuscinosis, late-degenerative stages of Down's syndrome, Alper's disease, vertigo as result of CNS degeneration, ALS, corticobasal degeneration, and progressive supranuclear palsy; pathologies associated with developmental retardation and learning impairments, Down's syndrome, and oxidative stress induced neuronal death; pathologies arising with aging and chronic alcohol or drug abuse including, for example, (i) with alcoholism, the degeneration of neurons in locus coeruleus, cerebellum, cholinergic basal forebrain, (ii) with aging, degeneration of cerebellar neurons and cortical neurons leading to cognitive and motor impairments, and (iii) with chronic amphetamine abuse, degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia, closed head trauma, and direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor). Preferably, the neurodegenerative disorder or cognitive deficit is dementia, Alzheimer's disease, Parkinson's disease, ALS or Hungtington's disease.

Accordingly, this invention also provides methods of treating mammals, preferably humans, for dementia or spinal cord injury which comprises the administration of the medicament or said pharmaceutical composition of this invention that contains a compound having formula as shown above.

In some embodiments, the effective amount of the compound of formula (I) administered to the subject is from about 1 to 100 mg/Kg body weight of the subject by intravenous, intramuscular injection or oral intake. The amount is administered to the subject by intravenous, intramuscular injection or oral intake at about 2, 3, 4, 5, 6, 7, 8, 9, 10, 20, 30, 40, 50, 60, 70, 80, 90 or 100 mg/Kg body weight of the subjec. In one embodiment, the subject is human and the administration amount if the compound is about 1 to about 50 mg/Kg body weight in a human; preferably about 1 to about 30 mg/Kg body weight in a human, preferably, about 1 to about 20 mg/Kg body weight, about 1 to about 10 mg/Kg body weight, about 2 to about 10 mg/Kg body weight, about 2 to about 8 mg/Kg body weight or about 2 to about 10 mg/Kg body weight; more preferably about 3 to about 5 mg/Kg body weight. The dose can be administered in a single aliquot, or alternatively in more than one aliquot.

In some embodiments, the method further includes the step of administering an agent that is known to improve the symptoms of neuronal injury, before, together with and/or after administering the compound of this invention. Examples of such agent include, but are not limited to, reactive oxygen scavenger (ROS), anticoagulant, neuronal enhancer, neuronal protective and the like, that are known in the art. Examples of reactive oxygen scavenger include, but are not limited to, catalase, superoxide dismutase (SOD), alpha-phenyl-N-tert-butylnitrone (PBN), vitamine E, vitamine C, polyphenolic compounds, carotenoids, and the like. Examples of anticoagulant include, but are not limited to, vitamine K, warfarin, acenocoumarol, heparin, aspirin, clopidogrel, dipyridamole, and the like.

This disclosure also provides a pharmaceutical composition for treating neuronal injury; the composition comprises a therapeutically effective amount of a compound having formula (I) as shown above; and a therapeutically acceptable excipient.

Generally, the compound having formula (I) of this invention is present at a level of about 0.1% to 99% by weight, based on the total weight of the pharmaceutical composition. In some embodiments, the compound having formula (I) of this invention is present at a level of at least 1% by weight, based on the total weight of the pharmaceutical composition. In certain embodiments, the compound having formula (I) is present at a level of at least 5% by weight, based on the total weight of the pharmaceutical composition. In still other embodiments, the compound having formula (I) is present at a level of at least 10% by weight, based on the total weight of the pharmaceutical composition. In still yet other embodiments, the compound having formula (I) is present at a level of at least 25% by weight, based on the total weight of the pharmaceutical composition.

In some embodiments, the medicament of said pharmaceutical composition of this invention further includes an agent that is known to improve the symptoms of dementia or spinal cord injury. Examples of such agent include, and are not limited to, reactive oxygen scavengers (ROS), anticoagulants, neuronal enhancer, neuronal protective and the like, that are known in the art. Examples of reactive oxygen scavenger include, but are not limited to, catalase, superoxide dismutase (SOD), alpha-phenyl-N-tert-butylnitrone (PBN), vitamine E, vitamine C, polyphenolic compounds, carotenoids, and the like. Examples of anticoagulant include, but are not limited to, vitamine K, warfarin, acenocoumarol, heparin, aspirin, clopidogrel, dipyridamole, and the like.

The medicament or said pharmaceutical composition is prepared in accordance with acceptable pharmaceutical procedures, such as described in Remington's Pharmaceutical Sciences, 17$^{th}$ edition, ed. Alfonoso R. Gennaro, Mack Publishing Company, Easton, Pa. (1985). Pharmaceutically acceptable excipients are those that are compatible with other ingredients in the formulation and biologically acceptable.

The compounds of this invention (e.g., the compound having formula (I) as shown above may be administered orally, parenterally, transdermally, rectally or by inhalation, alone or in combination with conventional pharmaceutically acceptable excipients. In preferred embodiments, the compounds of this invention are administered orally or parenterally to the subject.

The compounds of the present invention may be formulated into liquid pharmaceutical compositions, which are sterile solutions, or suspensions that can be administered by, for example, intravenous, intramuscular, subcutaneous, intraperitoneal injection or oral intake. Suitable diluents or solvent for manufacturing sterile injectable solution or suspension include, but are not limited to, 1,3-butanediol, mannitol, water, Ringer's solution, and isotonic sodium chloride solution. Fatty acids, such as oleic acid and its glyceride deratives are also useful for preparing injectables, as are natural pharmaceutically-acceptable oils, such as olive oil or castor oil. These oil solutions or suspensions may also contain alcohol diluent or carboxymethyl cellulose or similar dispersing agents. Other commonly used surfactants such as Tweens or Spans or other similar emulsifying agents or bioavailability enhancers that are commonly used in manufacturing pharmaceutically acceptable dosage forms can also be used for the purpose of formulation. Oral administration may be either liquid or solid composition form.

The medicament or said pharmaceutical compositions of this invention may be formulated into a variety of dosage forms for topical application. A wide variety of dermatologically acceptable inert excipients well known to the art may be employed. The topical compositions may include liquids, creams, lotions, ointments, gels, sprays, aerosols, skin patches, and the like. Typical inert excipients may be, for example, water, ethyl alcohol, polyvinyl pyrrolidone, propylene glycol, mineral oil, stearyl alcohol and gel-producing substances. All of the above dosages forms and excipients are well known to the pharmaceutical art. The choice of the dosage form is not critical to the efficacy of the composition described herein.

The medicament or said pharmaceutical compositions of this invention may also be formulated in a variety of dosage forms for mucosal application, such as buccal and/or sublingual drug dosage units for drug delivery through oral mucosal membranes. A wide variety of biodegradable polymeric excipients may be used that are pharmaceutically acceptable, provide both a suitable degree of adhesion and the desired drug release profile, and are compatible with the active agents to be administered and any other components that may be present in the buccal and/or sublingual drug dosage units. Generally, the polymeric excipient comprises hydrophilic polymers that adhere to the wet surface of the oral mucosa. Examples of polymeric excipients include, but are not limited to, acrylic acid polymers and copolymers; hydrolyzed polyvinylalcohol; polyethylene oxides; polyacrylates; vinyl polymers and copolymers; polyvinylpyrrolidone; dextran; guar gum; pectins; starches; and cellulosic polymers.

Such medicament or composition is administered to a mammal, preferably human, by any route that may effectively transports the active ingredient(s) of the composition to the appropriate or desired site of action, such as oral, nasal, pulmonary, transdermal, such as passive or iontophoretic delivery, or parenteral, e.g., rectal, depot, subcutaneous, intravenous, intramuscular, intranasal, intra-cerebral, ophthalmic solution or an ointment. Further, the administration of the compound of this invention with other active ingredients may be concurrent or simultaneous.

It will be appreciated that the dosage of compounds of the present invention will vary from patient to patient not only for the particular compound or composition selected, the route of administration, and the ability of the compound (alone or in combination with one or more drugs) to elicit a desired response in the patient, but also factors such as disease state or severity of the condition to be alleviated, age, sex, weight of the patient, the state of being of the patient, and the severity of the pathological condition being treated, concurrent medication or special diets then being followed by the patient, and other factors which those skilled in the art will recognize, with the appropriate dosage ultimately being at the discretion of the attendant physician. Dosage regimens may be adjusted to provide the improved therapeutic response. A therapeutically effective amount is also one in which any toxic or detrimental effects of the compound or composition are outweighed by the therapeutically beneficial effects. Preferably, the compounds or compositions of the present invention are administered at a dosage and for a time such that the number and/or severity of the symptoms are decreased.

The present invention will now be described more specifically with reference to the following embodiments, which are provided for the purpose of demonstration rather than limitation.

EXAMPLE

Example 1 Compound 1 Provides Neuronal Protective Activity to Subjects Suffering from Dementia Tg2576 transgenic mice carry a transgene coding for the 695-amino acid isoform of human APP derived from a large Swedish family with early-onset Alzheimer's disease (AD). These mice express high concentrations of the mutant Aβ, develop significant number of amyloid plaques and display memory deficits. To verify whether compounds of this invention possess any neuron protective effects, Tg2576 transgenic mice were treated with the test compound (e.g., compound 1) or vehicle, and the effect of the test compound(s) on brain function deficit and neuroplasticity were respectively measured by Contextual Fear Conditioning and Western blotting.

1.1 Preparation of Dementia Animal Model

Tg2576 transgenic mice carry a transgene coding for the 695-amino acid isoform of human APP derived from a large Swedish family with early-onset Alzheimer's disease (AD). These mice express high concentrations of the mutant Aβ, develop significant number of amyloid plaques and display memory deficits. Tg2576 mice were purchased from The Jackson laboratory (Maine, US). C57BL/6J mice 6-8 week of age were purchased from BioLASCO Taiwan Co., Ltd for dose-dependent effect study. The animals were housed 5 per cage in a temperature (21±1° C.)—and humidity (70±5%)—controlled room, under a 12 h-12 h light-dark cycle (lights on at 6:00 a.m.). Animal had free access to food and water during the experiment. Behavior testing was carried out in the light phase of the cycle. All animal experiments were carried out in accordance with the guidelines established by the Institutional Animal Care and Utilization Committee of the Taipei Medical University (Taipei, Taiwan, R.O.C.).

1.2 Preparation and Administration of Medicament

Compound 1 was dissolved in 5% ethanol, 35% polyethylene glycol and 60% normal saline at a concentration of 15 mg/ml. C57BL/6J Mice were treated with Compound 1 (50, 100, 200 mg/kg, intraperitoneally) or vehicle once before contexual fear conditioning training. Then, Tg2576 transgenic mice were treated with Compound 1 orally (50 mg/kg per day for 20 days) or vehicle at the ages of 5 months and 11 months.

1.3 Contextual Fear Conditioning

All mice were transported to the laboratory for 2 hour before training to erase unnecessary stress. Tru Scan Photo Beam Tracking system (Coulbourn Instruments, New York, US) was used in this study. In the behavioral training, mice were placed in the chamber and after 2 minutes received two conditioned stimulus (CS; 80 dB auditory sound, 30 seconds) pairing with unconditioned stimulus (US; 0.7 mA mild footshock, 2 seconds) at 2 minutes interval. 24 hours later, the freezing behavior was test subsequently to measure the strength of tone-shock associated memory equally placed in the training chamber. On test day, mice were exposed to context alone during 3 minutes, and following by 3 minutes CS presentation. The data was recorded and calculated by its system software (TruScan 2.02).

1.3 Sample Preparation, Protein Extraction and Western Blotting

Animals were deep anesthetized with choral hydrate (400 mg/kg) and perfused with both normal saline and 4% paraformaldehyde. The hippocampus were collected and lysed in lysis buffer (Lysis-M reagent, Roche). The lysates were incubated for 5 min on ice and centrifuged for 20 min at 14,000 r.p.m. and 4° C. The supernatant was collected as cytosolic protein extract. Protein concentrations were measured and normalized using Bradford protein assay kit (Pierce). After normalization, 30 μg of protein was subjected to western blotting. Immunoreactivity was examined by enhanced chemiluminescence (Millipore).

1.4 Results

FIG. 1 depicts the effect of compound 1 on enhancement of memory formation in normal C57BL/6J mice with dose dependent significance. Freezing behavioral test after 24 h contextual fear conditioning training represented the strength of tone-shock pairing memory increased significantly (*p<0.05, p<0.01; n=8, 9, 8 and 8, respectively). It is evident from FIG. 1** that compound 1 of this invention is effective on Freezing behavioral test even in normal mice.

Figure 2:
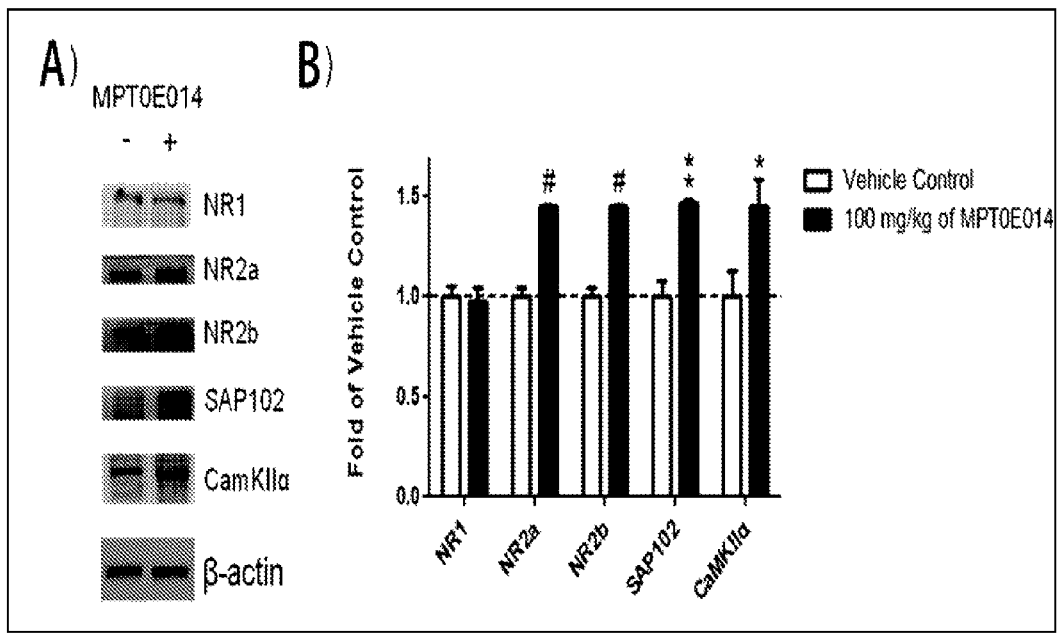
FIG. 2 illustrates the effect of compound 1 on up-regulation of memory-related protein in accordance with one embodiment of this invention.

FIG. 2 depicts the effect of compound 1 on up-regulation of memory-related protein 24 hours after intraperitoneal injection of 100 mg/kg of compound 1. A, Sample from hippocampal extraction showed that protein level changes in compound 1-treated mice. B, Quantitative data represented significant difference between vehicle and compound 1 treatment (*p<0.05, **p<0.01, #p<0.001).

Figure 3:
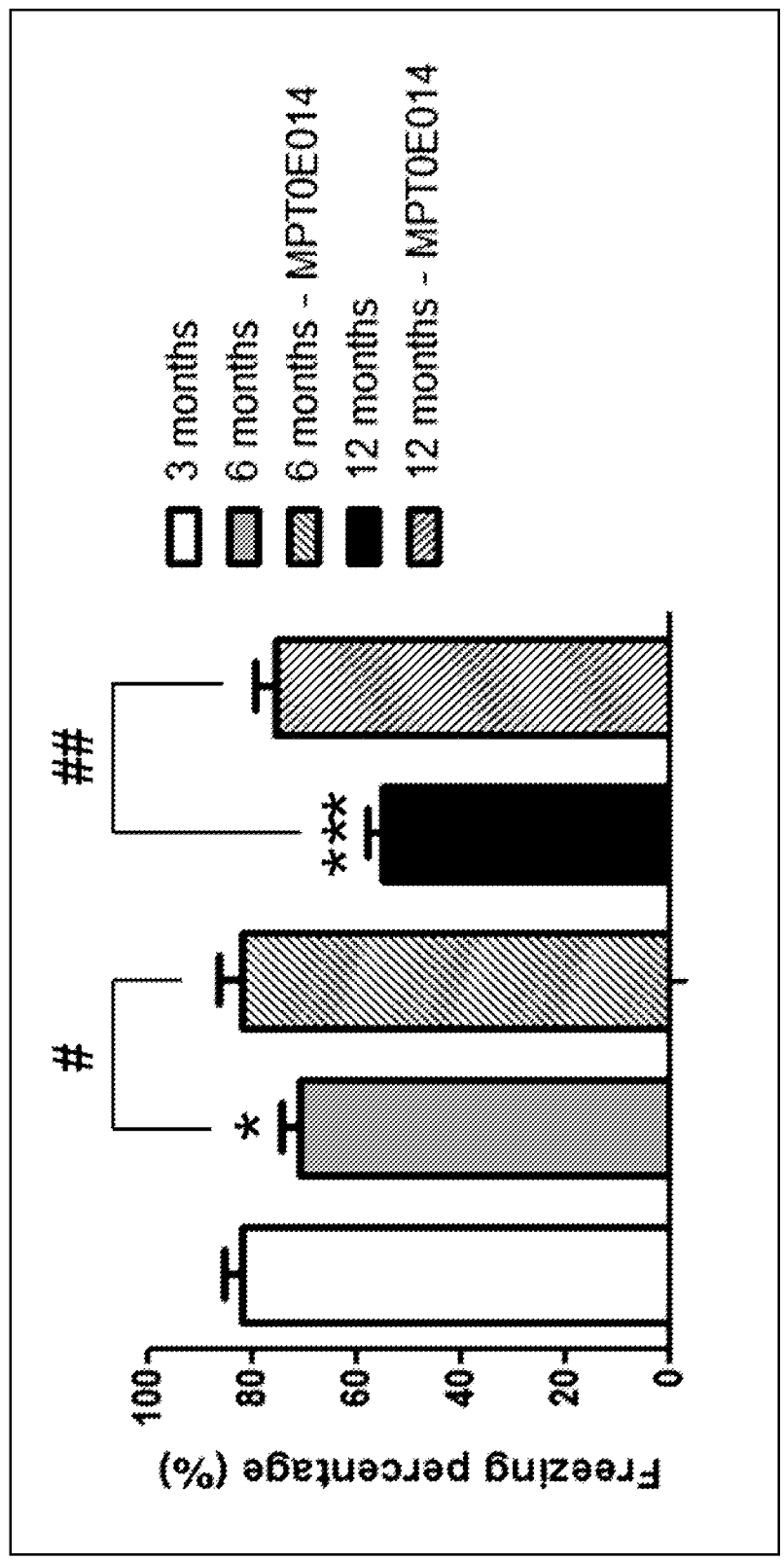
FIG. 3 illustrates the effect of compound 1 on contextual fear conditioning while conditioned stimulus-unconditioned stimulus (CS-US) pairing demonstrated the motor function and cognition in Tg2576 mice in accordance with one embodiment of this invention.

FIG. 3 depicts the effect of compound 1 on contextual fear conditioning while CS-US pairing demonstrated the motor function and cognition in Tg2576 mice. The tone-shock pairing memory of Tg2576 mice (n=7, 7, 6, 5, 3 and 5 respectively) were enhanced by treatment with Compound 1 orally (50 mg/kg per day for 20 days) (6-month old v.s. 6-month old—compound 1 treated, *p=0.0264) and retarded by aged-related amnesia (3-month old v.s. 6-month old, *p=0.0152; 3-month old v.s. 12-month old, ***p=0.0005; 6-month old v.s. 6-month old—compound 1 treated, #p=0.0264; 12-month old v.s. 12-month old—compound 1 treated, ##p=0.0028).

Figure 4:
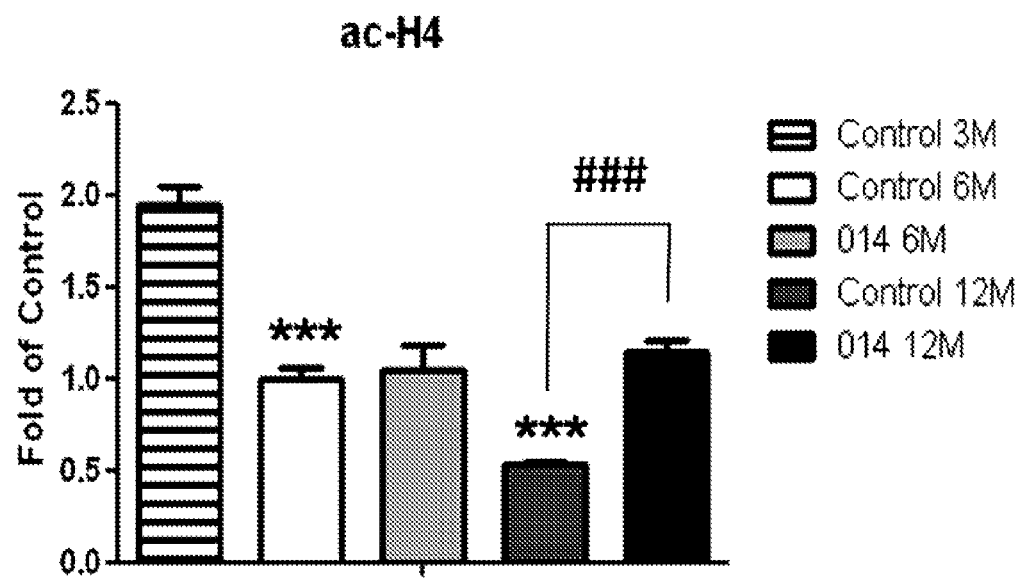
FIG. 4 illustrates the effect of oral treatment with compound 1 (50 mg/kg per day for 20 days) on the expression of synaptic plasticity proteins level attenuated by age-related changes in hippocampus of Tg2576 mice in accordance with one embodiment of this invention.
Figure 4:
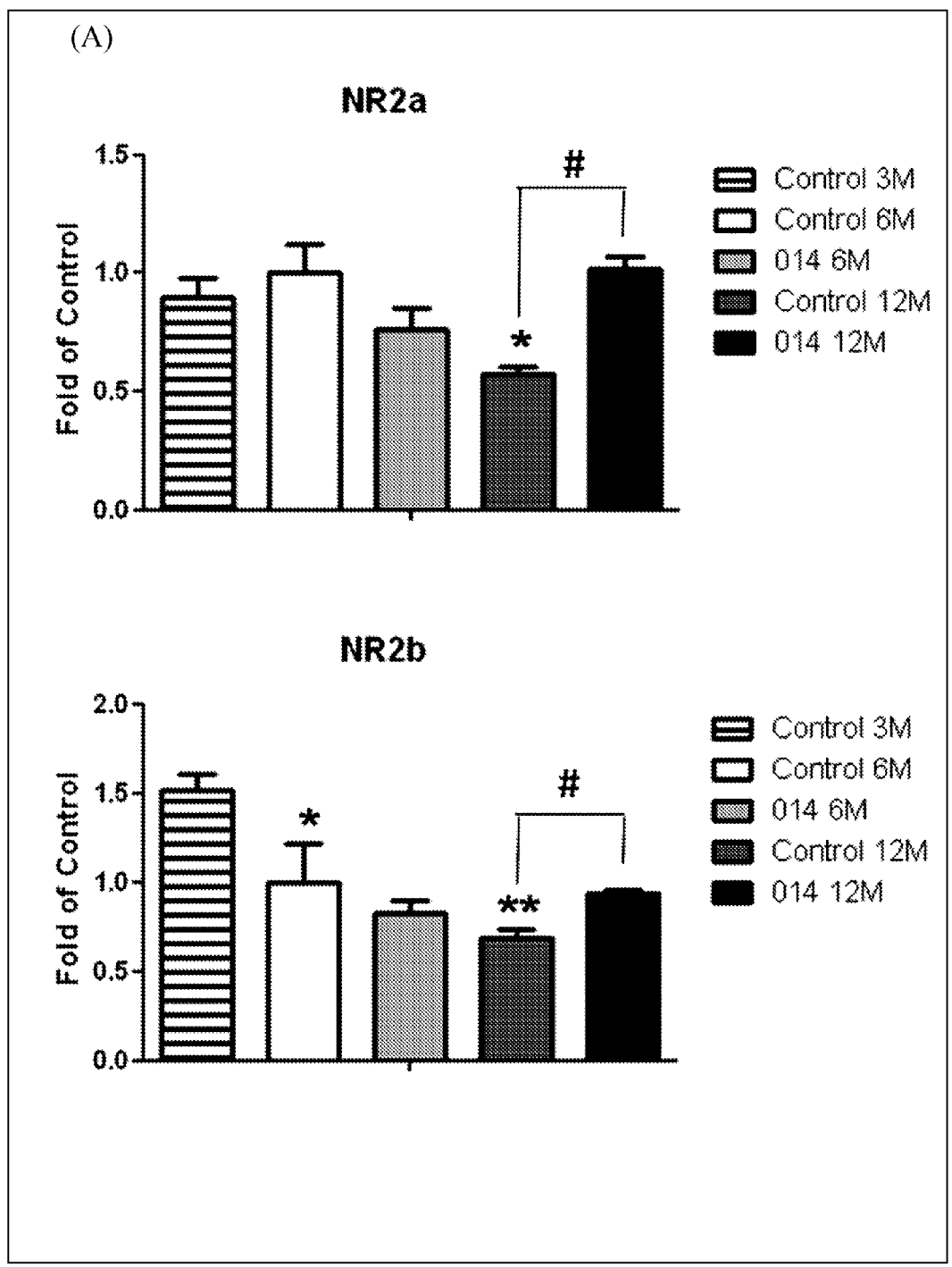
Figure 4:
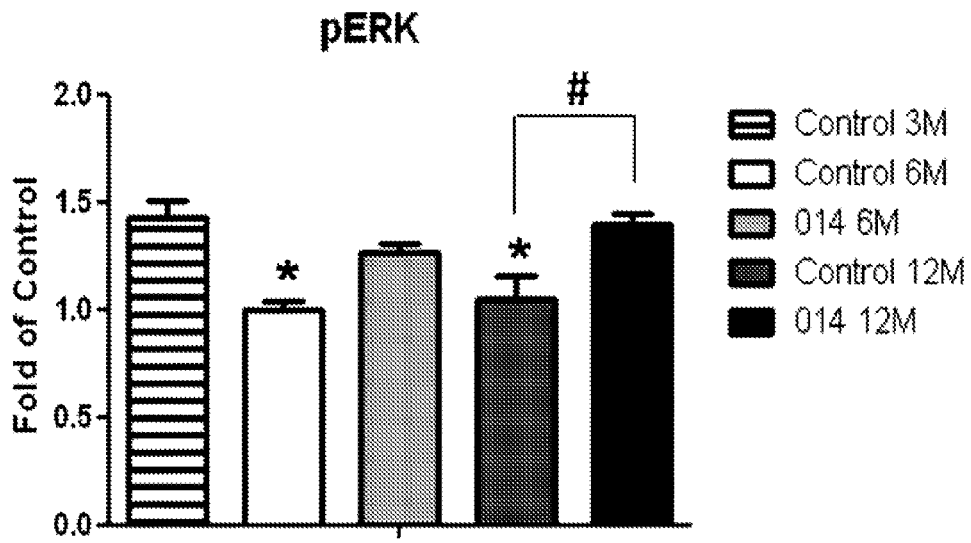
Figure 4:
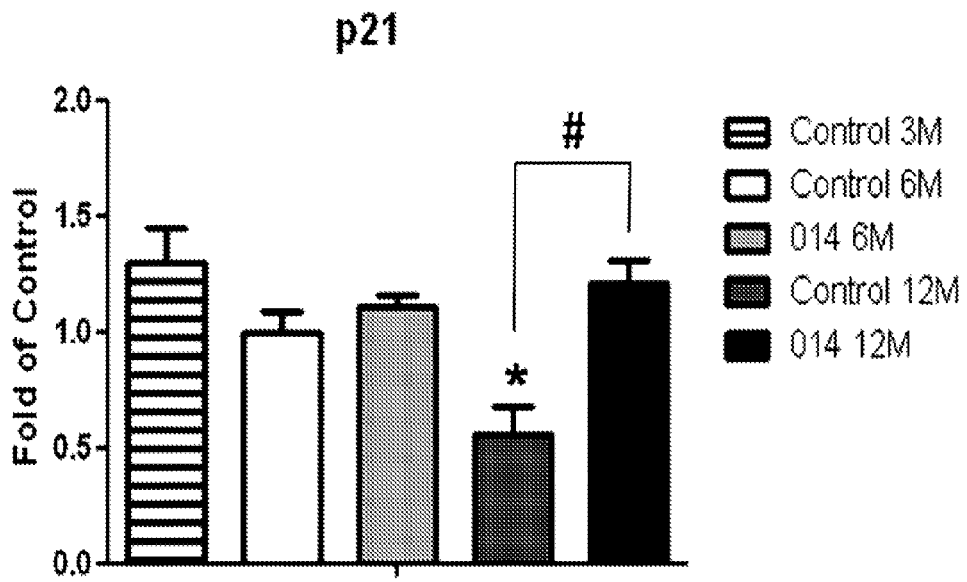

FIG. 4 depicts the effect of oral treatment with compound 1 (50 mg/kg per day for 20 days) on the expression of synaptic plasticity proteins level attenuated by age-related changes in hippocampus of Tg2576 mice. A, The subunit of NMDA receptor, NR2a and NR2b protein expression were degraded from age (left: compare with 3-month-old mice, *p=0.0226; right: *p=0.0477; **p=0.0012) and elevated after compound 1 oral gavage (left: #p=0.0231; right: #p=0.0492), as well as B, pERK, the active form of transcriptional and translational marker anti-apoptotic marker (compare Control 3M with Control 6M, *p=0.0165; and Control 12M, *p=0.0486; #p=0.0428), C, p21, anti-apoptotic marker (*p=0.0175; #p=0.0145), and D, acetyl-Histone H4 (compare Control 3M with Control 6M, *p=0.0007; and Control 12M, *p=0.0002; ###p=0.0008).

Example 2 Compound 1 Provides Neuronal Protective Activity to Subjects Having Spinal Cord Injury In this example, effects of compounds of this invention were verified using spinal cord injury animal model. Similar to procedures described in Example 1, animals were artificially induced to produce spinal cord injury and then treated with the test compound 1 or vehicle, and the effect of the test compound on behavio score, neural preservation and anti-apoptosis were respectively measured by Basso, Beattie, and Bresnahan (BBB) Locomotor Rating Scale, immunohistochemistry (IHC) staining and western blot analysis.

2.1 Preparation of Spinal Cord Injury Animal Model

Male Sprague-Dawley rats (Academia Sinica, Taiwan), weighing 280-330 g, were kept two per cage for at least five days after their arrival. The rats had access to food and water at libitum and were housed within a room with a 12:12 h dark-light cycle. This study was performed in accordance with the guidelines provided by the Experimental Animal Laboratory and approved by the Animal Care and Use Committee in Taipei Medical University.

The spinal cord injury was produced by using the NYU (New York University) impactor device. The spinal cord contusion was performed under deep anesthesia with Zoleti150 (40 mg/kg i.p.) After a dorsal laminectomy was performed on T9, the spinal cord segments T9 were exposed. Then, the surgery of spinal cord injury was produced by dropping the 10 gram rod from a height of 50 mm. The contusion injury resulted in hind limb locomotor deficits.

Motor Behavior Test

Behavioral tests and analyses were performed by observers blinded to the treatments. Locomotor function was observed and recorded using the Basso, Beattie, and Bresnahan (BBB) Locomotor Rating Scale. On days 1, 3, and 7 post injury, hindlimb motor function was assessed using the open-field BBB score locomotor test.

2.3 Preparation and Administeration of Medicament

Compound 1 was dissolved in 5% ethanol, 35% polyethylene glycol and 60% normal saline at a concentration of 15 mg/ml. All test animals received intravenous injection of either compound 1 (30 mg/Kg per day for 7 days), or vehicle (5% ethanol, 35% polyethylene glycol and 60% normal saline) at 1-7 days after spinal cord injury.

Histology, Immunohistochemistry and Cell Count

On 7th day after hemisection spinal cord injury, animals were deeply anesthetized by isoflurane and perfused through the left ventricle with phosphate-buffered saline (PBS), followed by cold 4% paraformaldehyde in 0.15M sodium phosphate buffer, pH 7.4. The spinal cord was removed immediately, postfixed for 8 h in the same fixative at 4° C., and cryoprotected for 2-3 days in 15% and 30% sucrose. The spinal cord was frozen in powdered dry ice and stored at −80° C. until needed. Five micrometers sections were cut with a freezing and sliding microtome at the center of spinal cord hemisection. The sections were prepared for either for immunostaining or apoptosis staining. For immunohistochemistry, sections were washed in PBS and incubated in 3% normal goat serum with 0.3% Triton X-100 in PBS for 1 h. The sections were incubated free-floating at 4° C. with anti-NeuN (neuron-nuclear specific protein) (Chemicon, Temecula, Calif.). Immunoreactivity was visualized using the Vectastain Elite ABC Peroxidase method (Vector Laboratories, Burlingame, Calif.) and diaminobenzidine (DAB) as the chromagen. Furthermore, apoptosis after spinal cord injury was detected by terminal deoxynucleotidyl transferase-mediated deoxyuridine triphosphate nick-end labeling (TUNEL) using the apoptosis detection kit (Oncogene Research Products, Cambridge, Mass.). TUNEL staining was performed according to the manufacturer's instructions. A negative control of TUNEL staining was generated by omission of Klenow enzyme, while negative control sections of other immunohistochemical studies were incubated as above without primary antibodies. Cell counting was performed on every sixth section at the center of spinal cord hemisection stained with the above antibodies at a magnification of ×400. Only cells with clearly visible stain were counted. All data are presented as means±SEM of five consecutive cell quantifications.

Results

Figure 5:
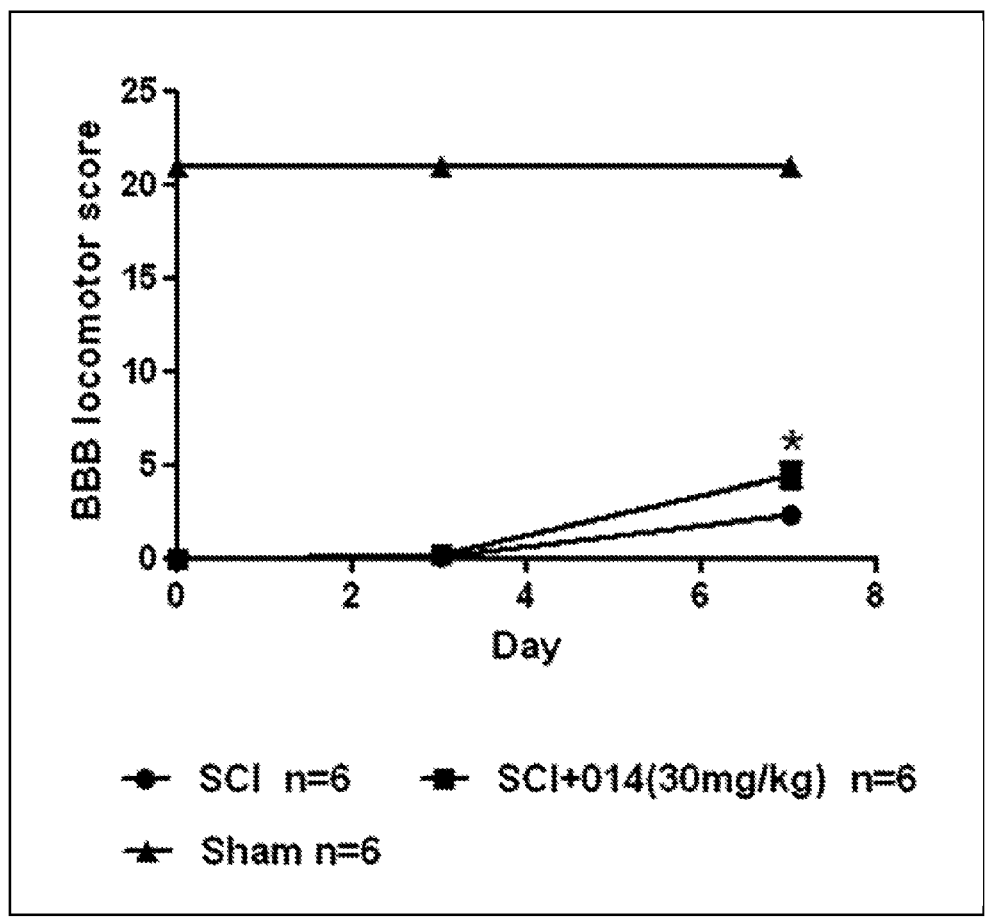
FIG. 5 illustrates the effect of compound 1 on recovery of the motor function in accordance with one embodiment of this invention.

FIG. 5 depicts the effect of compound 1 on recovery of the motor function by BBB score. After intravenous injection of compound 1 (30 mg/Kg per day for 7 days), the treated rats had significant recovery of BBB score compares with vehicle group 7 days after spinal cord injury. (p=0.0147, n=6 in each group)

Figure 6:
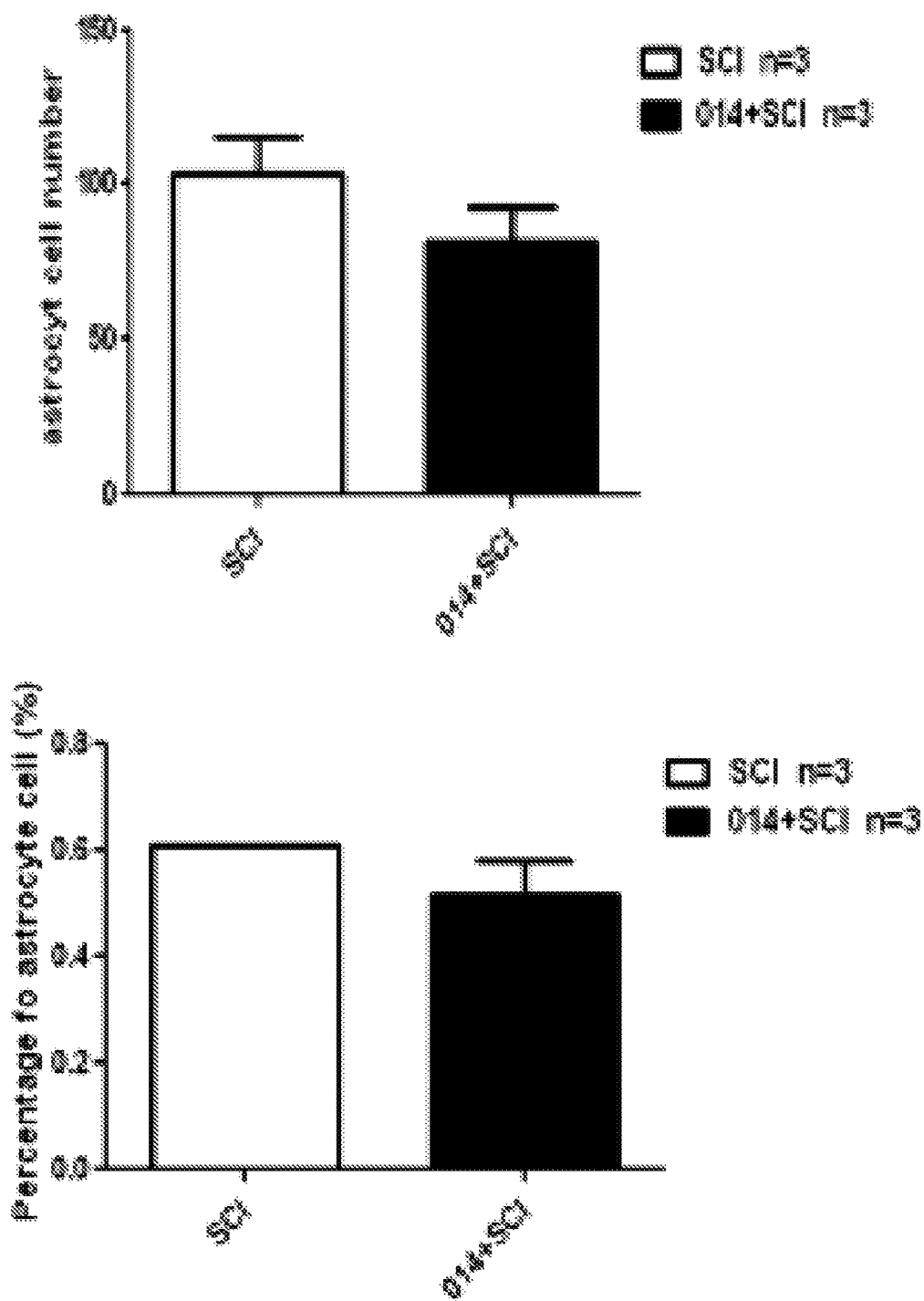
FIG. 6 illustrates the effect of compound 1 on preservation of neuronal loss after spinal cord injury in accordance with one embodiment of this invention.
Figure 6:
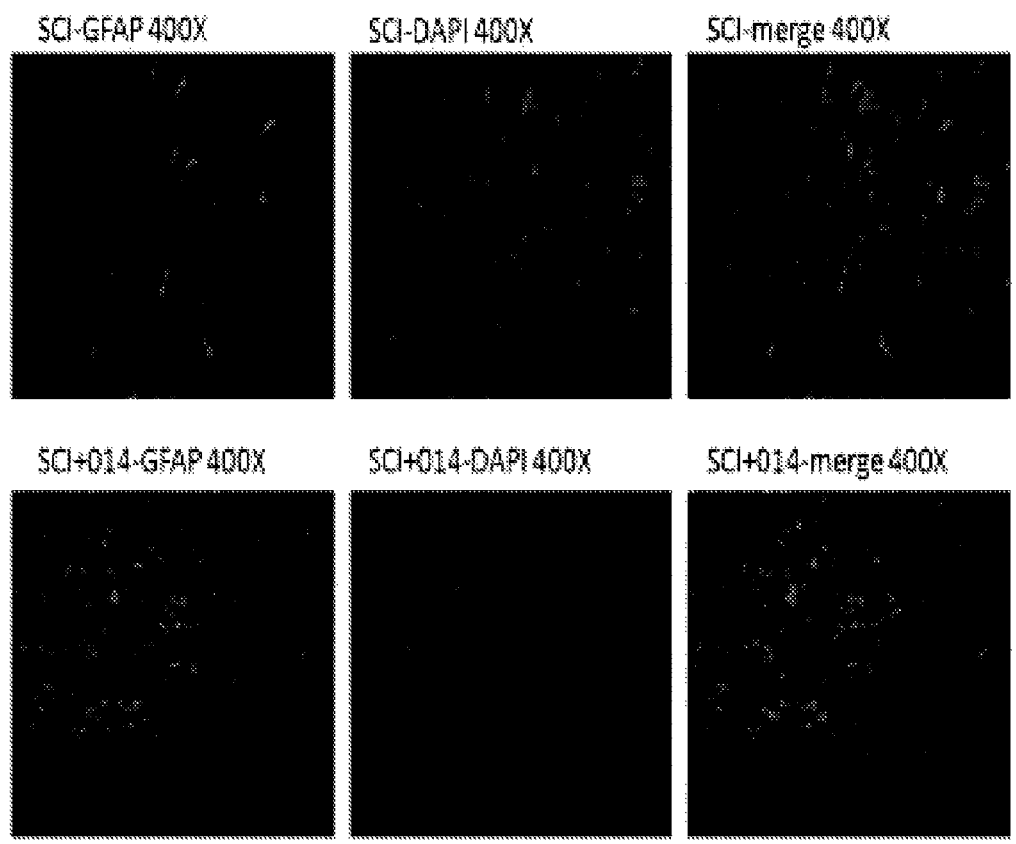

FIG. 6 depicts the effect of compound 1 on preservation of neuronal loss after spinal cord injury. Immunohistochemistry of NeuN, neuron-specific marker, disclosed severe neuron loss in the vehicle group, while significantly preserved in the compound 1 treated group (30 mg/Kg per day for 7 days). (p<0.0001 in neuron cells percentage and p=0.0151 in neuron cells number, n=3 in each group, 400×).

Figure 7:
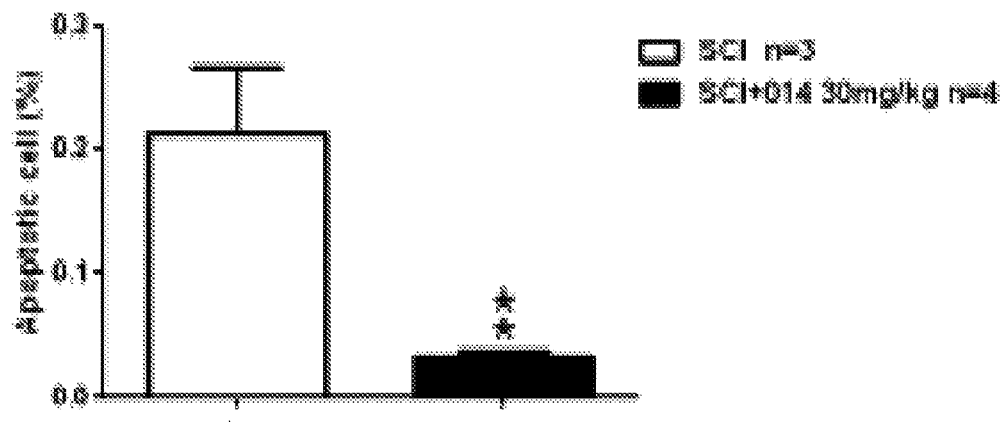
FIG. 7 illustrates the effect of compound 1 on anti-apoptosis after spinal cord injury in accordance with one embodiment of this invention.
Figure 7:
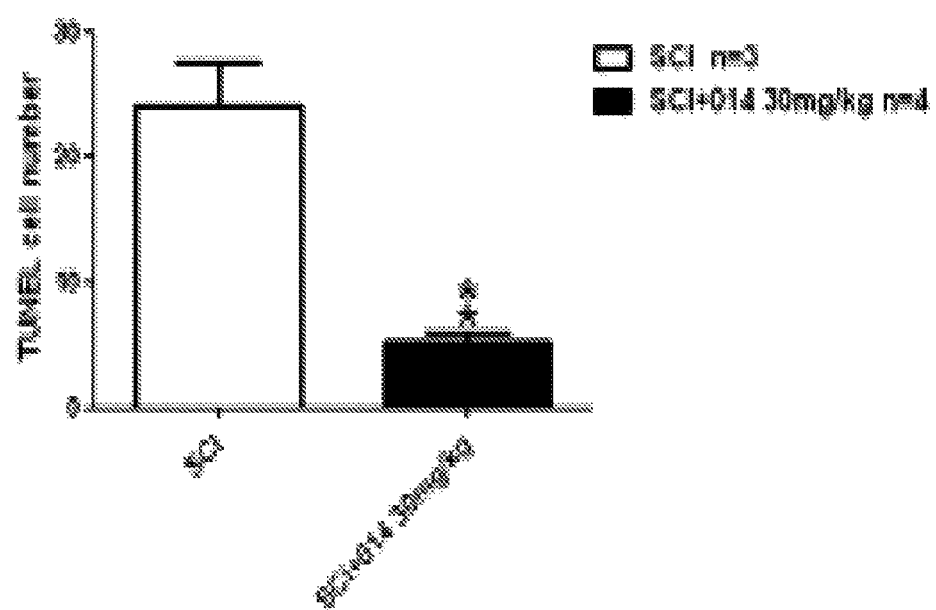
Figure 7:
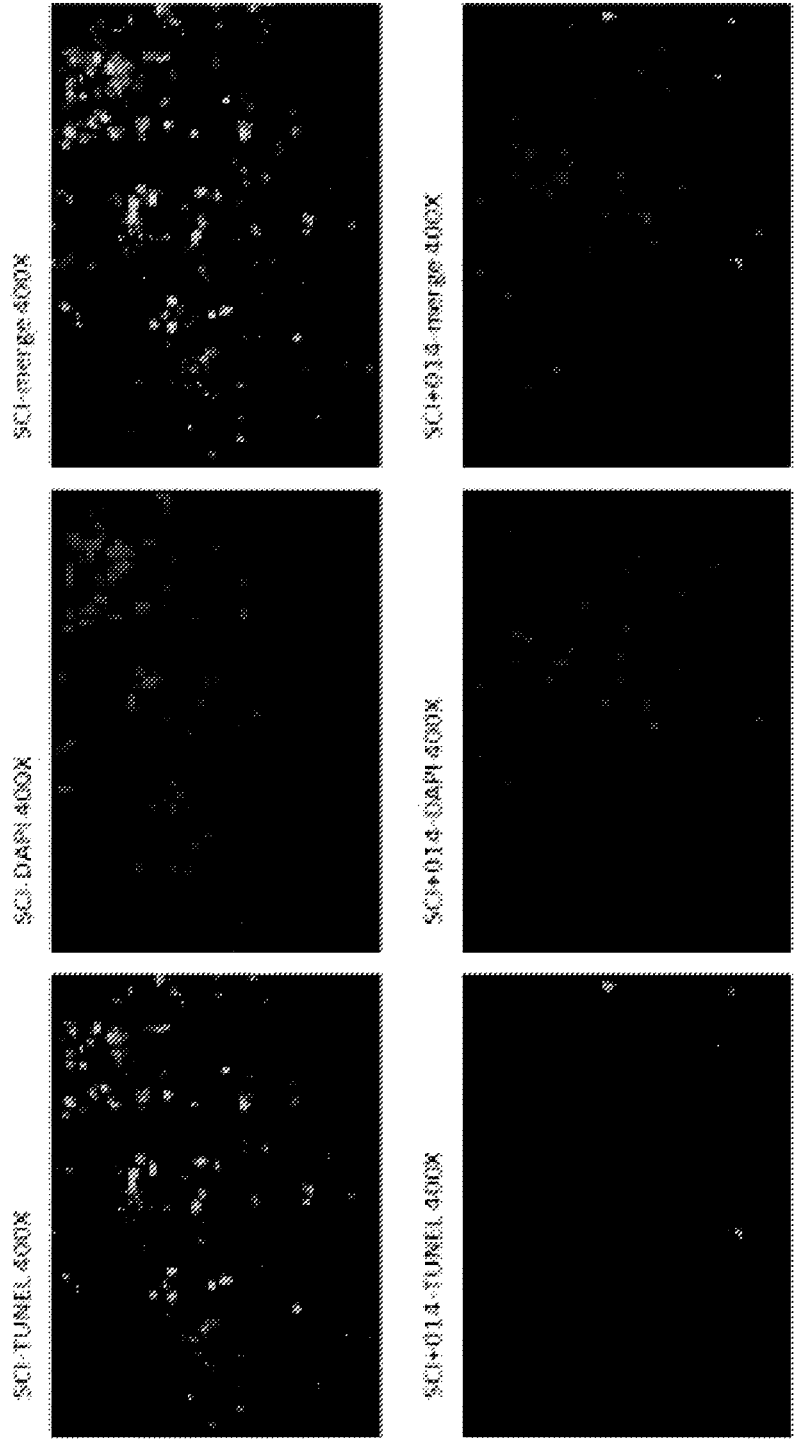

FIG. 7 depicts the effect of compound 1 on anti-apoptosis after spinal cord injury. TUNEL staining showed marked increase of apoptotic cells in the vehicle group, while significantly reduced in the compound 1 treated group (30 mg/Kg per day for 7 days). (p=0.0098 in apoptotic cells percentage and p=p=0.0015 in apoptotic cells number, n=3 in each group, 400×).

Figure 8:
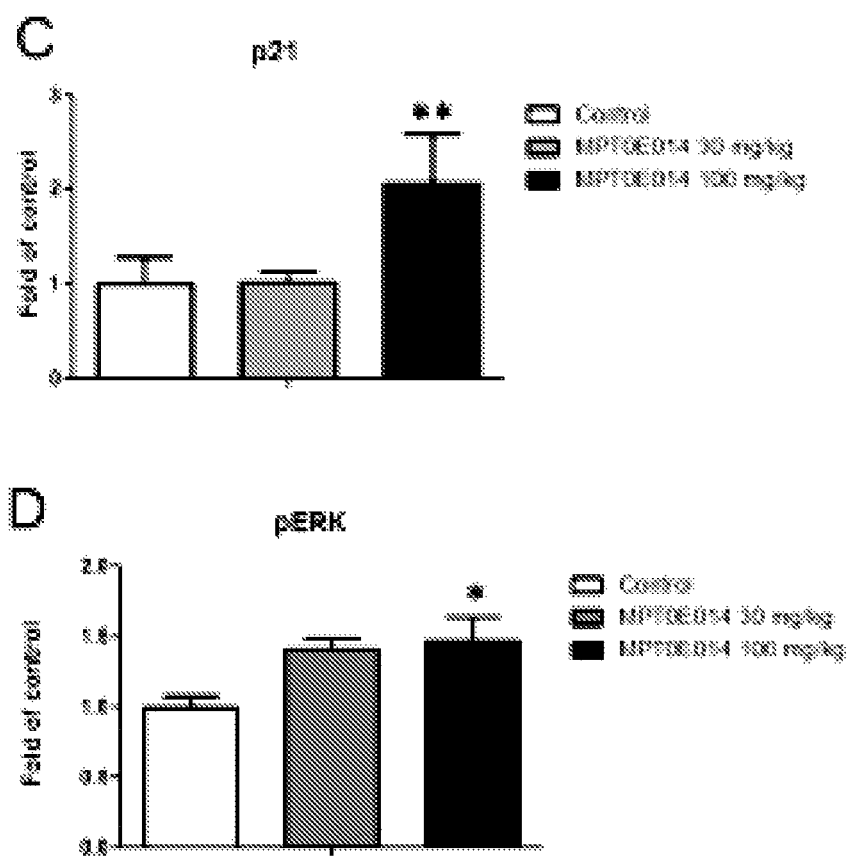
FIG. 8 illustrates the effect of compound 1 on expression of histone 3 and 4 acetylation, p21 and phospho-ERK after spinal cord injury with one embodiment of this invention.
Figure 8:
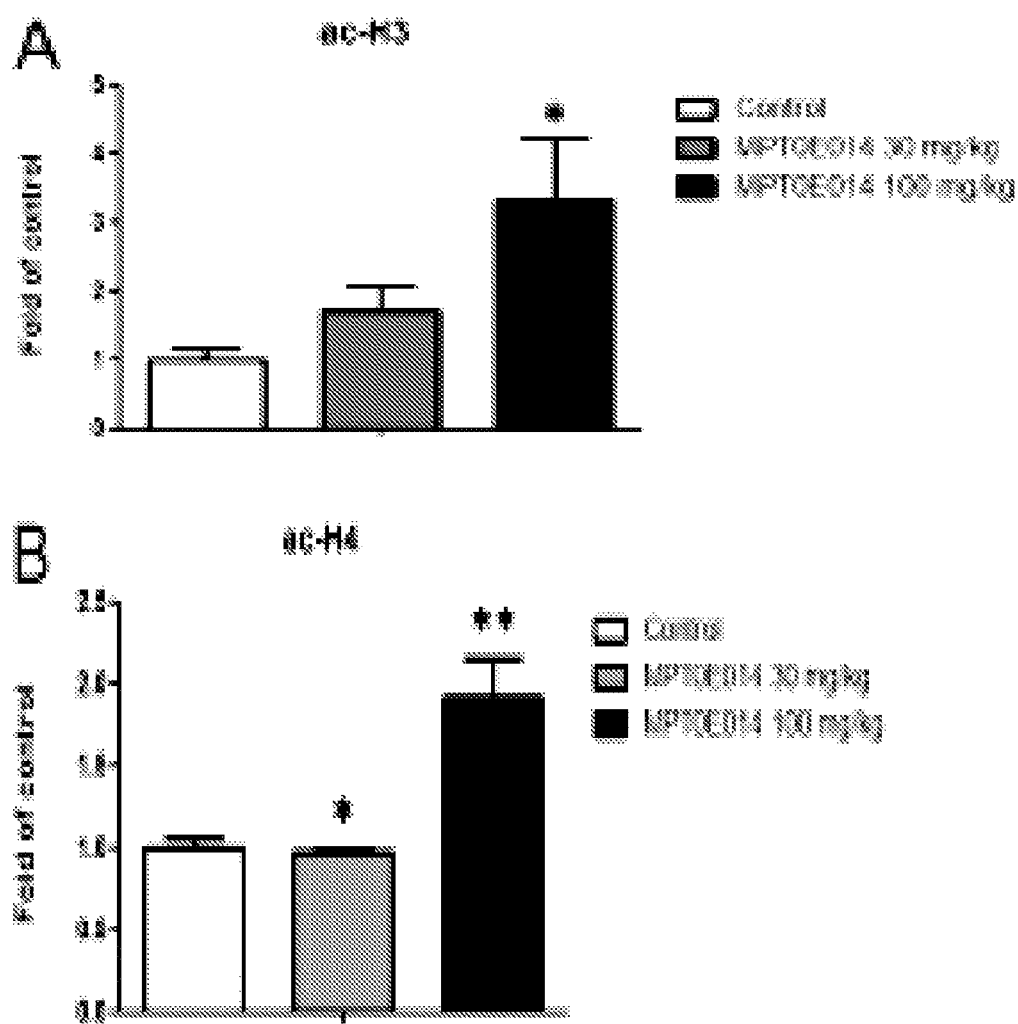

FIG. 8 depicts the effect of compound 1 (30 mg/kg, 100 mg/kg, intravenous injection) on expression of histone 3 and 4 acetylation, p21 and phospho-ERK after spinal cord injury. Significant increase of expression of histone 3 and 4 acetylation, p21 and phospho-ERK was noted at the dosage of 100 mg/kg compared with vehicle control group. (ac-H3 p=0.0451, ac-H4 p=0.0023, p21 p=0.0043, p-ERK p=0.0311, n=5 in each group).

What is claimed is:

1. A method for reducing neuronal loss and increasing locomotor function after spinal cord injury in a subject, comprising administering to the subject a therapeutically effective amount of the compound having formula (I),

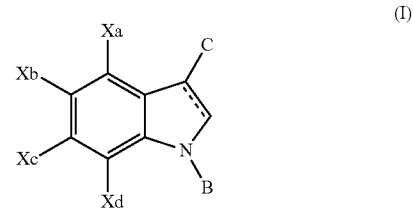

wherein ═══ is a single or double bond; B is SO$_2$R; C is H; X$_a$, X$_c$ and X$_d$ are H; X$_b$ is CH═CHC(O)NHOH; and R is H, alkyl, alkenyl, alkynyl, aryl, or heteroaryl or a pharmaceutically acceptable salt thereof.

2. The method of claim 1, wherein R is phenyl or phenyl substituted by F.

3. The method of claim 1, wherein the compound of formula (I) is selected from the following compounds,

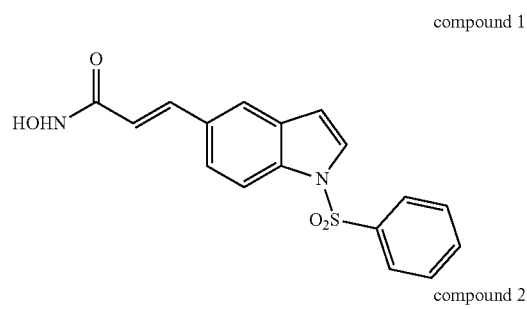

compound 1

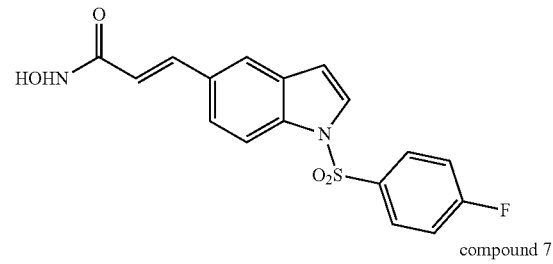

compound 2

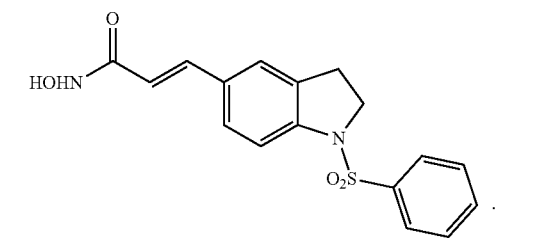

compound 7

4. The method of claim 1, wherein the compound of formula (I) is 3-(1-benzensulfonyl-1H-indol-5-yl)-N-hydroxy-acrylamide.

5. The method of claim 1, wherein the compound of formula (I) administered to the subject is from about 1 to 100 mg/Kg body weight of the subject.

6. The method of claim 1, wherein the compound of formula (I) administered to the subject is from 1 to about 50 mg/Kg body weight in a human.

7. The method of claim 1, wherein the compound of formula (I) of claim 1 is administered orally or parenterally to the subject.

8. The method of claim 1, wherein the subject is human.

9. The method of claim 1, wherein the method further includes the step of administering an additional agent to improve the symptoms of neuronal injury, wherein the additional agent is selected from the group consisting of a reactive oxygen scavenger (ROS), an anticoagulant agent, a catalase, a superoxide dismutase (SOD), alpha-phenyl-N-tert-butylnitrone (PBN), vitamin E, vitamin C and a carotenoid.

10. The method of claim 9, wherein the additional agent can be administered before, together with and/or after administering the compound of claim 1.

11. The method of claim 9, wherein the anticoagulant agent is vitamin K, warfarin, acenocoumarol, heparin, aspirin, clopidogrel, or dipyridamole.

* * * * *